(12) United States Patent
Malish

(10) Patent No.: US 11,793,456 B2
(45) Date of Patent: Oct. 24, 2023

(54) TREATMENT USING INDIVIDUALIZED TRANSCRANIAL MAGNETIC STIMULATION

(71) Applicant: WellBrain LLC, Canyon Lake, TX (US)

(72) Inventor: Shannon Lea Malish, Spring Branch, TX (US)

(73) Assignee: WellBrain LLC, Canyon Lake, TX (US)

( * ) Notice: Subject to any disclaimer, the term of this patent is extended or adjusted under 35 U.S.C. 154(b) by 436 days.

(21) Appl. No.: 17/143,716

(22) Filed: Jan. 7, 2021

(65) Prior Publication Data

US 2022/0211325 A1    Jul. 7, 2022

(51) Int. Cl.
| | |
|---|---|
| A61B 5/00 | (2006.01) |
| A61N 2/00 | (2006.01) |
| A61B 5/374 | (2021.01) |
| G16H 20/70 | (2018.01) |
| A61B 5/291 | (2021.01) |
| A61N 2/02 | (2006.01) |

(52) U.S. Cl.
CPC ............ *A61B 5/4836* (2013.01); *A61B 5/291* (2021.01); *A61B 5/374* (2021.01); *A61N 2/006* (2013.01); *A61N 2/02* (2013.01); *G16H 20/70* (2018.01)

(58) Field of Classification Search
None
See application file for complete search history.

(56) References Cited

U.S. PATENT DOCUMENTS

| | | |
|---|---|---|
| 6,066,163 A | 5/2000 | John |
| 8,926,490 B2 | 1/2015 | Phillips et al. |
| 9,015,057 B2 | 4/2015 | Phillips et al. |
| 10,029,111 B2 | 7/2018 | Jin |
| 10,420,482 B2 | 9/2019 | Jin |
| 10,420,953 B2 | 9/2019 | Jin |
| 11,311,741 B2 | 4/2022 | Phillips et al. |
| 2011/0130615 A1 | 6/2011 | Mishellevich |

(Continued)

FOREIGN PATENT DOCUMENTS

WO    2013/172981    11/2013

OTHER PUBLICATIONS

P.G. Janicak et al., "Transcranial magnetic stimulation for the treatment of major depression," Neuropsychiatr. Dis. Treat., vol. 11, pp. 1549-1560, Jun. 26, 2015.

(Continued)

*Primary Examiner* — Christine H Matthews
(74) *Attorney, Agent, or Firm* — FOX ROTHSCHILD LLP

(57) ABSTRACT

Systems and methods for providing predictive diagnostics for mental health diagnosing by utilizing quantitative electroencephalography measurements of an individual to diagnose or assist in the diagnosis of a neurological or mental disease state for that individual. The diagnosed mental state can then be treated utilizing individualized transcranial magnetic stimulation, which balances deficits in the brain whether caused by organic damage, physical damage, or emotional/trauma damage. The individualized transcranial magnetic stimulation repairs these areas of the brain with customized protocols unique to the patient's brain based upon the quantitative electroencephalography measurements made during the diagnosis.

16 Claims, 9 Drawing Sheets

(56) References Cited

U.S. PATENT DOCUMENTS

2014/0058189 A1 2/2014 Stubbeman
2018/0256912 A1* 9/2018 Leuchter .............. A61B 5/7242

OTHER PUBLICATIONS

P.G. Janicak et al., "The Efficacy of Transcranial Magnetic Stimulation for Major Depression: A Review of the Evidence," Psychiatric Annals, vol. 44, No. 6, pp. 284-292, Jun. 24, 2014.
"Transcranial magnetic stimulation," Wikipedia, 17 pages, retrieved from https://en.wikipedia.org/w/index.php?title=Transcranial_magnetic_stimulation&oldid=971762254, last edited Aug. 8, 2020.

* cited by examiner

PRIOR ART

TREATMENT USING INDIVIDUALIZED TRANSCRANIAL MAGNETIC STIMULATION

TECHNICAL FIELD

This invention relates to individualized transcranial magnetic stimulation, and more particularly to diagnosing and treatment of particular disease states in neurology and mental health.

BACKGROUND

Mental disorders can present as painful, debilitating, and very costly for the affected individual and their family. The lack of treatment often leads to debilitating and life-threatening consequences. The standard method of diagnosing mental disorders has been with either the Diagnostic and Statistical Manual of Mental Disorders 5th edition ("DSM-5") or the International Statistical Classification of Diseases and Related Health Problems ("ICD"). Both standards primarily involve diagnosis through a mental health provider's personal interview with the patient regarding symptoms and behaviors. As such, both the interviewer and the patient may introduce their own subjective bias into the process. Furthermore, the patient may not accurately report due to perceived negative implications.

As a result, there is a desire for better techniques of diagnosing and treating mental disorders, including alcohol and substance abuse disorders, based on measurable objective data.

DETAILED DESCRIPTION

Figure 1:
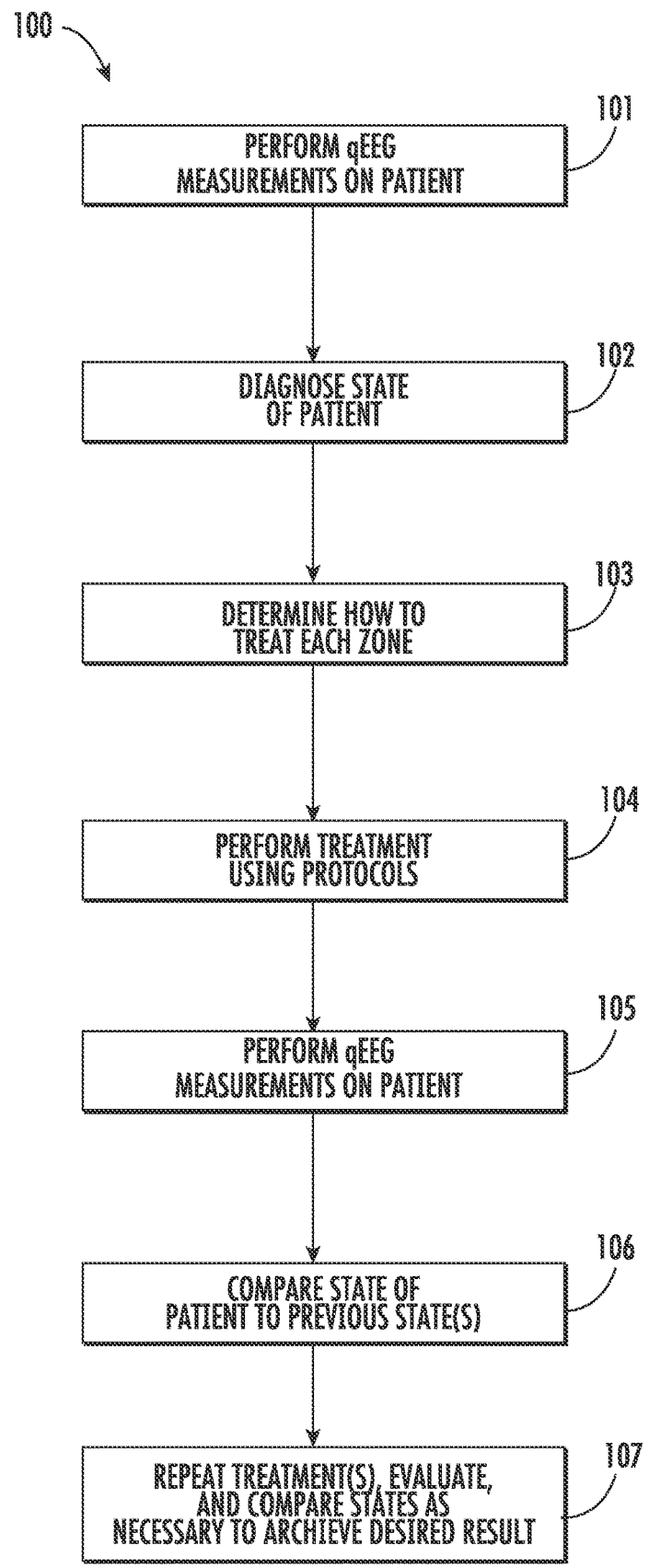
FIG. 1 illustrates a flowchart diagram configured in accordance with embodiments of the present disclosure.

The brain is an integrated command center that has 86 million neurons. When these neurons are out of sync, the condition is referred to as brain arrhythmia, which has been proven to be the cause for many brain-related diseases and abnormal conditions. Embodiments of the present disclosure diagnose any brain arrhythmia within a patient's brain and provide treatment to bring the frequencies in all areas of the brain back in balance to promote mental wellness. By analyzing EEG scans and optional psychometric assessments, embodiments of the present disclosure create an individualized plan for Transcranial Magnetic Stimulation to align neurons in different parts of the brain to work synchronously in the same frequency.

The following definitions will be used in describing embodiments of the present disclosure:

Transcranial Magnetic Stimulation ("TMS"): A noninvasive form of brain stimulation by applying a changing magnetic field to cause electric current at a specific area of the brain through electromagnetic induction used to treat Depression, Migraine, and OCD.

Quantitative electroencephalography ("qEEG"): An analysis of digitized EEG measurements taken on a patient during an EEG examination. In lay terms, this is also referred to as "Brain Mapping" (three-dimensional).

Channel: An EEG electrode capturing brainwave activity (i.e., EEG measurements).

Zone: Different selected regions of the brain for which brainwave activity is measured. Such zones may be selected to correspond to the EEG electrode channels utilized in the 10-20 system, which is an internationally recognized method to describe and apply the location of scalp electrodes in the context of an EEG examination/scan.

Homeostatic Frequency: The Homeostatic Frequency is the Alpha wave frequency at which a brain operates as measured by the qEEG. This frequency may vary at different zones of the brain. A normal Homeostatic Frequency should lie between 8 Hz-12 Hz.

Alpha brainwaves are dominant during quietly flowing thoughts, and in some meditative states. Alpha is the resting state for the brain. Alpha waves aid overall mental coordination, calmness, alertness, mind/body integration, and learning. For purposes in accordance with certain embodiments of the present disclosure, an optimal "Homeostatic" Alpha wave frequency for a particular patient is also referred to herein as the "Target Frequency."

Greatest Frequency: The frequency at which most of the neurons fire during the period of conducting an EEG examination. This is the frequency with the maximum PSD (as defined herein) for each channel.

Pulse: A single magnetic stimulation with a TMS system.

Train: The period (seconds) of magnetic stimulation required for the Pulse Rate.

Pulse Rate: The number of Pulses in a Train.

InterTrain: The period (seconds) of pause between Trains.

Amplitude: The power setting prescribed for magnetic stimulation. The higher the Amplitude, the stronger the stimulation.

Power Spectrum/Spectral Density ("PSD"): A Power Spectral Density is the measure of a signal's power (voltage) content versus frequency. A PSD is typically used to characterize broadband random signals. The amplitude of the PSD may be normalized by the spectral resolution employed to digitize the signal.

The power spectrum $S_{xx}(f)$ of a time series $x(t)$ describes the distribution of power into frequency components composing that signal. According to Fourier analysis, any physical signal can be decomposed into a number of discrete frequencies, or a spectrum of frequencies over a continuous range. The statistical average of a certain signal or sort of signal (including noise) as analyzed in terms of its frequency content, is called its spectrum.

When the energy of the signal is concentrated around a finite time interval, especially if its total energy is finite, one may compute the energy spectral density. More commonly used is the power spectral density (or simply, power spectrum), which applies to signals existing over all time, or over a time period large enough (especially in relation to the duration of a measurement) that it could as well have been over an infinite time interval. The PSD then refers to the spectral energy distribution that would be found per unit time, since the total energy of such a signal over all time would generally be infinite. Summation or integration of the spectral components yields the total power (for a physical process) or variance (in a statistical process), identical to what would be obtained by integrating $x^2(t)$ over the time domain, as dictated by Parseval's theorem. See Marc-Antoine Parseval des Chênes, "Mémoire sur les séries et sur l'intégration complète d'une équation aux différences partielles linéaire du second ordre, à coefficients constants," presented before the Académie des Sciences (Paris) on Apr. 5, 1799. This article was published in "Mémoires présentés à l'Institut des Sciences, Lettres et Arts, par divers savants, et lus dans ses assemblées. Sciences, mathématiques et physiques. (Savants étrangers.)," vol. 1, pp. 638-648 (1806), which is hereby incorporated by reference herein.

During the course of conducting an EEG examination, at each channel the PSD for a frequency is a measure of how many times brainwaves of that frequency were observed. It can be thought of as relative power or dominance of that frequency.

To compute the homeostatic brain-wave frequency, the average power of a signal in a specific frequency range (e.g., 2-20 Hz) is calculated, which includes computing a single number that summarizes the contribution of the given frequency to the overall power of the signal. This implies the decomposition of the EEG measurement signal into frequency components, which is achieved through a Fast Fourier Transform. Then the magnitude-squared of the FFT is taken to obtain an estimate of the PSD.

Embodiments of the present disclosure utilize the Welch Method to compute the PSD, which includes averaging consecutive Fourier transform of small windows of the signal, with or without overlapping. See P. D. Welch, "The Use of Fast Fourier Transform for the Estimation of Power Spectra: A Method Based on Time Averaging Over Short, Modified Periodograms," IEEE Transactions on Audio and Electroacoustics, Vol. AU-15, No. 2, June, 1967, which is hereby incorporated by reference herein.

The EEG measurement signal can be represented as sequence of data values or samples:

$x[0], x[1], \ldots, x[N-1]$

The data sequence ranges from 0 to N−1. The data values x[n] are indexed by their sample number n. This is the sample value's position relative to the start of the sequence. The data samples are acquired at a constant rate. The time between two successive data samples x[n] and x[n+1] is T seconds. The sample rate is 1/T samples per second. The length of the data sequence in seconds is $T_{seq}=N*T$. The time of acquisition of a data value is related to its sample number by $t=t_0+nT$ where to is time when the first data sample was acquired.

The procedure to calculate PSD can be mathematically described by the following steps:

1. EEG data sequence:

$x[0], x[1], \ldots, x[N-1]$

Is partitioned into K segments or batches:
Segment 1: x[0], x[1], . . . , x[M−1]
Segment 2: x[S], x[S+1], . . . , x[M+S−1]
:
Segment K: x[N−M], x[N−M+1], . . . , x[N−1]
where,
M=Number of points in each segment or batch
S=Number of points to shift between segments
K=Number of segments or batches 2. For each segment (k=1 to K), compute a windowed Discrete Fourier Transform ("DFT") at some frequency $$v = i/M \text{ with} -\left(\frac{M}{2}-1\right) \le i \le \frac{M}{2}:$$

$$X_k(v) = \sum_m x[m]w[m]e^{-j2\pi vm}$$

Where, $m = (k-1)S, \ldots, M + (k-1)S - 1$, and $w[m]$ = the window function (taper function).

3. For each segment (k=1 to K), form the modified periodogram value, $P_k(f)$, from the discrete Fourier transform:

$$P_k(v) = \frac{1}{W}|X_k(v)|^2$$

$$\text{Where, } W = \sum_{m=0}^{M} w^2[m]$$

4. Average the periodogram to obtain estimate of PSD:

$$S_x(v) = \frac{1}{K}\sum_{k=1}^{K} P_k(v)$$

Welch's method is also called the Weighted Overlapped Segment Averaging ("WOSA") method and periodogram averaging method. The parameter M is the length of each segment. Note that M is the length of the DFT. The parameter S is the number of points to shift between segments. It is the number of new points in each segment or batch. The number of points in common to two adjacent segments is M−S. Two adjacent segments are said to overlap by M−S points or 100[(M−S) M]%.

A FFT is a fast algorithm for computing the DFT in Step 2 of the above method. The M-point sequence w[m] is the window function. Some common windows are the rectangular, Hann, Hamming, Blackman, Blackman-Harris, and Kaiser-Bessel.

The squaring and averaging may be performed in the frequency domain in Steps 3 and 4. Step 3 forms the periodogram or sample spectrum.

The units for $P_k(v)$ are the same as those for $S_x(v)$, i.e., $V^2/Hz$. The $P_k(v)$ may not be good estimates of PSDs because they may contain too much statistical oscillation. Step 4 averages the periodograms $P_k(v)$ to form a stable PSD estimate that does not oscillate wildly.

In accordance with embodiments of the present disclosure, exemplary parameters utilized for the above steps may be:

In Step 1, take 256 points at a time (M=256), and shift the window by 128 points (S=128). Thus, two adjacent segments overlap by 50%. The shift between segments S is usually in the range 0.4M<S<M.

In Step 2, take Hann as the window function, since it yields improved sensitivity specificity and reduced spectral leakage.

In accordance with embodiments of the present disclosure, the unit of PSD is converted from $V^2/Hz$ to $\mu V^2/Hz$.

Embodiments of the present disclosure provide predictive diagnostics for mental health diagnosing by providing systems and methods for utilizing qEEG measurements of an individual to diagnose or assist in the diagnosis of a neurological or mental disease state for that individual. Embodiments of the present disclosure further provide systems and methods for utilizing individualized transcranial magnetic stimulation ("iTMS") to treat the diagnosed state.

Embodiments of the present disclosure are applicable to the diagnosis and treatment of all neurological or mental disease states (for the sake of simplicity, these will be simply referred to herein as "mental states"), including, but not limited to, Major Depressive Disorder ("MDD"), addictions of various types, anxiety, sleep disorders, substance abuse, traumatic brain injury/concussion, Attention Deficit Hyperactivity Disorder ("ADHD"), issues associated with menopause, executive functions, early onset Dementia, eating disorders, tinnitus, anger problems, short-term memory loss, Obsessive-Compulsive Disorder ("OCD"), migraines, improvement of athletic performance, balance problems, and other brain disorders. Embodiments of the present disclosure may be utilized for inpatient and outpatient centers or by a therapeutic practitioner specializing in addiction, anxiety, depression, Bipolar Disorder, ADHD, sleep disorders, chronic pain, and other mental health and neurological disorders.

As described herein, embodiments of the present disclosure provide systems and methods to diagnose and/or treat the emotional and psychological health of a patient through the use of iTMS, which balances deficits in the brain, whether caused by organic damage, physical damage, or emotional/trauma damage. Embodiments of the present disclosure "repair" these areas of the brain with customized protocols unique to the patient's brain based upon one or more qEEG measurements made during the diagnosis.

Referring to FIG. 1, there is illustrated systems and methods 100 configured in accordance with embodiments of the present disclosure. In the process block 101, qEEG measurements are performed on a patient in a manner as further described herein. In the process block 102, the results of the qEEG measurements are used solely or in combination with other evaluation techniques to diagnose the patient for one or more mental states. In the process block 103, the diagnosis determined in the process block 102 will be used to determine how to treat selected zones using an iTMS system. In the process block 104, the iTMS system is utilized to perform the treatments determined in the process block 103 in accordance with one or more predetermined protocols. At some designated time after the performed treatments, another set of qEEG measurements are performed on the patient to determine how such qEEG measurements have changed due to the treatment performed in the process block 104. In accordance with certain embodiments of the present disclosure, one or more additional evaluation techniques may be performed to assess the progress of the mental state(s) of the patient. In the process block 106, the current mental presentation of the patient is compared to one or more previously determined mental states in order to evaluate and analyze how the previous treatment(s) have affected the diagnosed mental state(s) of the patient. The process block 107 represents that any one or more of the process blocks 101-106 may be repeated in order to achieve a desired result (e.g., change) in the mental state(s) of the patient.

Figure 6:
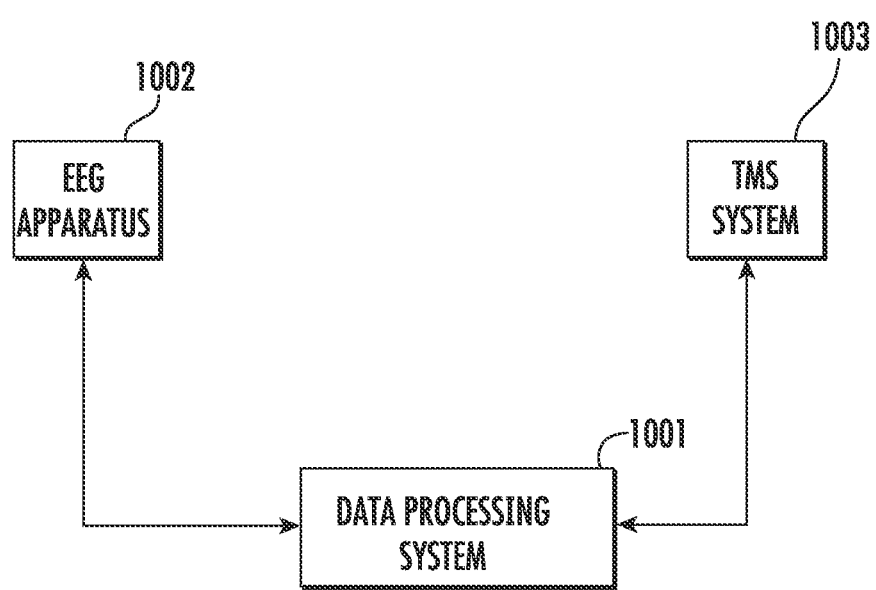
FIG. 6 illustrates a block diagram configured in accordance with embodiments of the present disclosure.

The EEG examinations/scans performed in the systems and methods 100 may be performed utilizing any well-known apparatus suitable for doing so (e.g., see the EEG apparatus 1002 of FIG. 6 described herein). For example, individually placed electrodes or a cap having pre-positioned electrodes may be applied to the patient's head in accordance with the 10-20 system.

Figure 2:
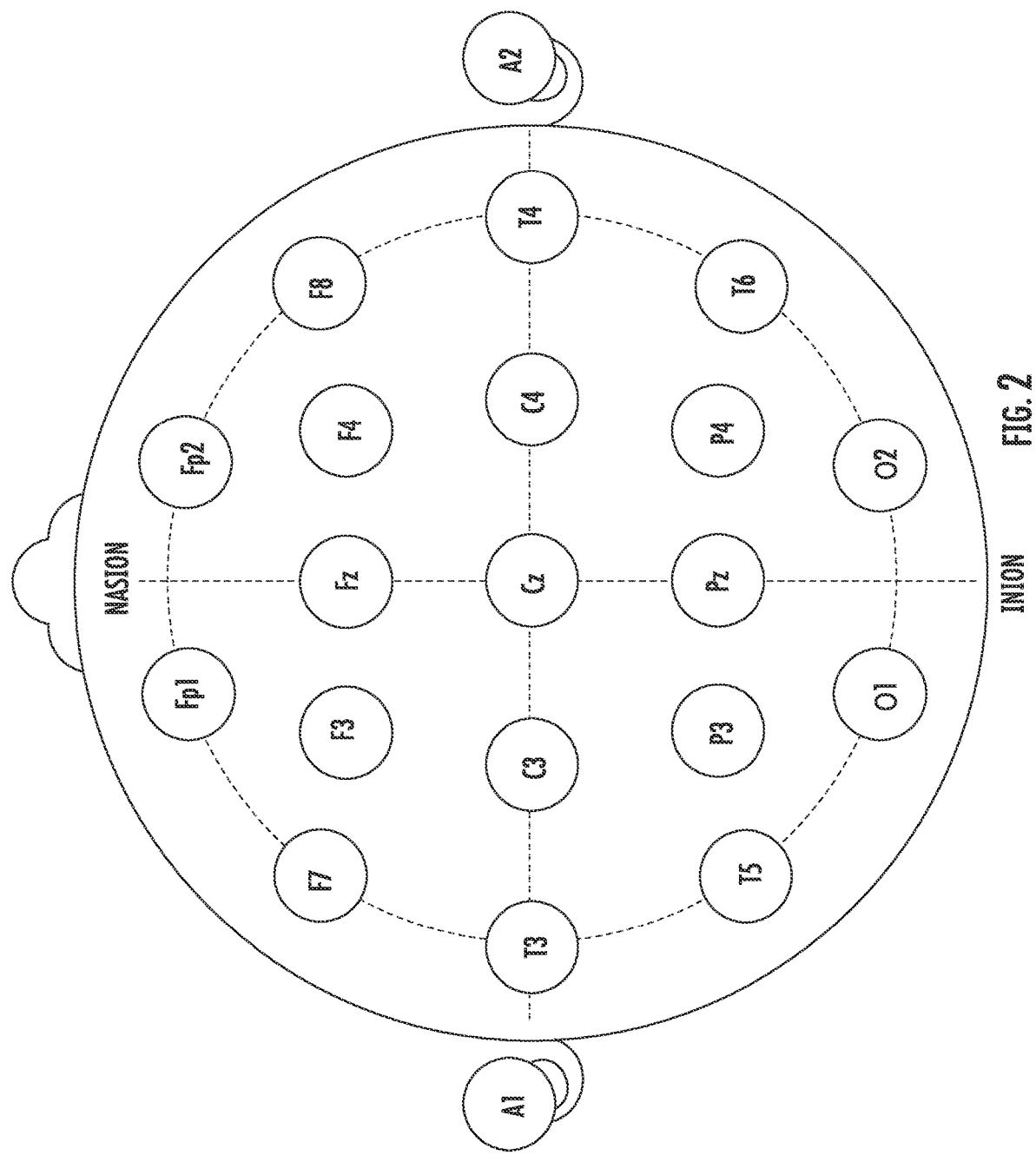
FIG. 2 illustrates EEG electrodes/channels according to the 10-20 system of electrode placement.

Referring to FIG. 2, there is illustrated the electrode labeling for such a 10-20 system. It has been determined that the electrodes can be utilized to analyze the following common functions in a patient, but are not limited to:

Fp1—Situational awareness, judgement, vigilance, irritability, depression, foggy headedness, disorganization, analytical area Fp2—Impulsivity (restraint of impulses), decision control, perseveration, social awareness, manic and panic behavior, emotional inhibition, avoidance behaviors, tactlessness Fz—Execution functions, linear tasks, working memory, absent mindedness, personality changes, intention and motivation F3—Verbal impulse control, motor planning, short-term memory, planning and problem solving, facial recognition, deducting facts to conclusions F4—Judgement and planning, motor planning ("makes the plan"), short-term memory, spatial-object memory, inductive creative, attentional area F7—Language, reading comprehension, verbal expression, working memory (visual and auditory), word retrieval, semantics, divided and selective attention F8—Emotional availability, emotional expression (anger, joy, happiness), sustained attention, conscious facial emotional processing Cz—Primary somatosensory, gross motor function C3—Right-sided somatosensory; fine motor skills, i.e., hand and digits (with F3, handwriting), feeling of pain, pressure, warmth C4—Left-sided somatosensory; fine motor skills, feeling of pain, pressure, warmth T3—Verbal memory and reading comprehension, long-term memory (verbal and visual), "inner voice" positive mood, auditory processing, sound perception, thyroid T4—Emotional memory, auditory processing, sound perception, anger, sadness, thyroid Pz—Visual memory, cognitive processing, dreaming, self-awareness P3—Cognitive Processing (verbal reasoning), depth perception, excessive thinking, integration of self-imagination, spelling, math calculations, complex grammar (right side of body awareness)

P4—Visuospatial memory, analytical skills, self-concern, map orientation, music, body image, knowing difference between right and left, (left side body awareness)

P7—Secondary visual processing, night vision

P8—Secondary visual processing, color, shapes

O1—Primary visual processing, visual acuity

O2—Primary visual processing, visual acuity, depth perception

A1, A2—Ear Clip Reference Points for heart rate

Note that not all areas and functions of the brain are ubiquitous for all patients.

In accordance with embodiments of the present disclosure, these mapped functions may be utilized to diagnose a mental state of a patient, and to depict the progress made with respect to a patient as they proceed through treatment protocols as described herein.

Figure 3A:
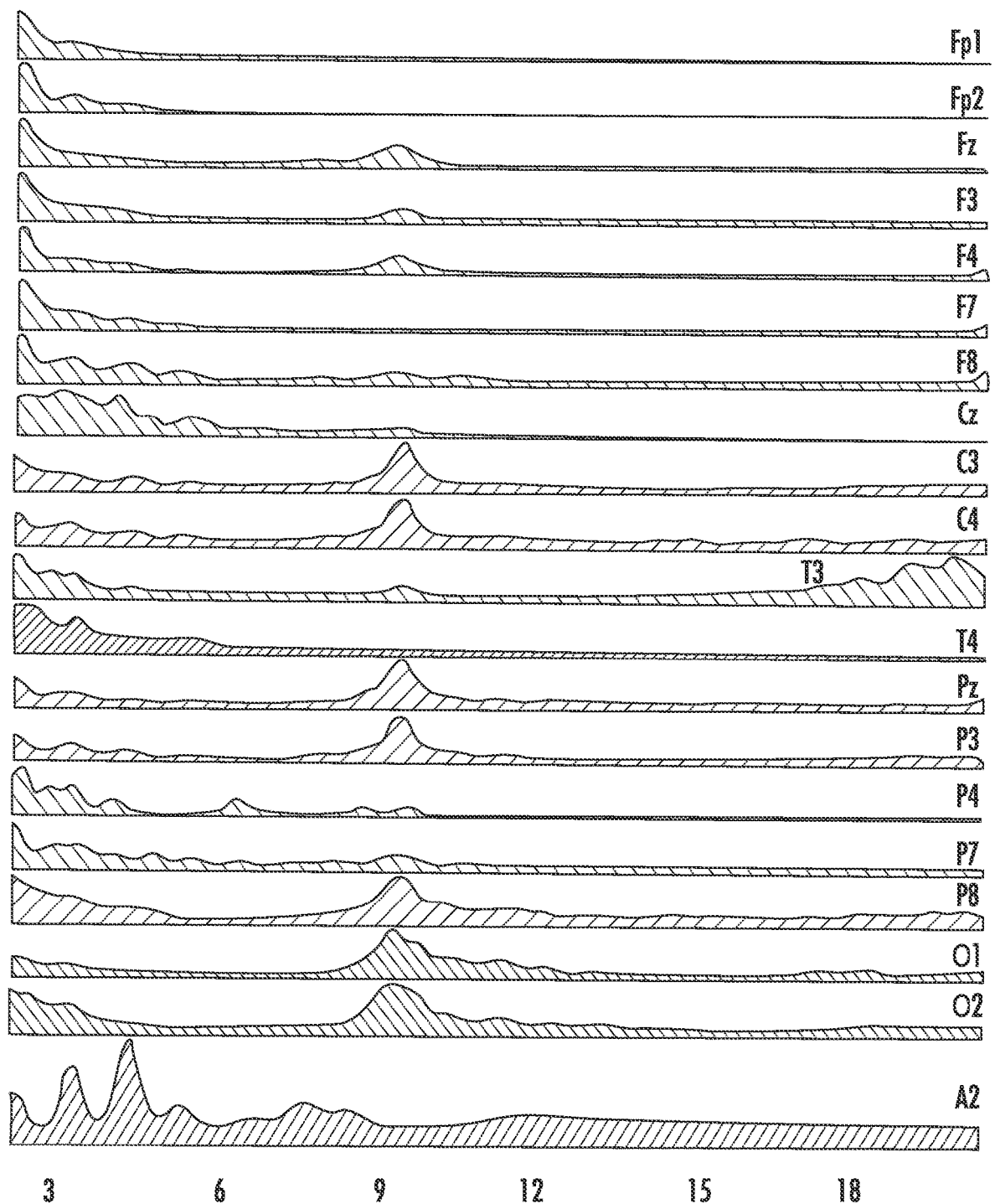
FIGS. 3A-3B illustrate a non-limiting example of qEEG Reports produced from EEG measurements taken on a sample patient. For each area of the brain (e.g., the locations corresponding to the EEG electrodes), a graph is produced. The x-axis represents the frequencies of brain activity. The y-axis represents the power/voltage of the measured signal. Each point on the graph represents the power generated at a specific frequency.

FIG. 3A illustrates a non-limiting example of a qEEG Report in which EEG measurements were taken on a sample patient, such as would be performed in the process block 101. Each of the PSD plots in the qEEG Report depicts the recorded PSD values on the y-axis and measured brain-wave frequencies (Hz) on the x-axis corresponding to each of the EEG electrodes. During the course of the qEEG measurements, the PSD of a frequency is a measure of how many times brainwaves of that frequency were observed.

As described herein, a healthy brain should exhibit a Greatest Frequency (i.e., the maximum PSD) for each channel in the range of 8-12 Hz (i.e., within the alpha wave region), and should be substantially the same (i.e., substantially aligned) for all channels. This means that all neurons in the brain should be synchronously firing with substantially the same frequency falling within the alpha wave region. Though this is true for some of the channels in the exemplary qEEG Report in FIG. 3A, not all of the channels exhibit the Greatest Frequency within the alpha wave region.

Figure 3B:
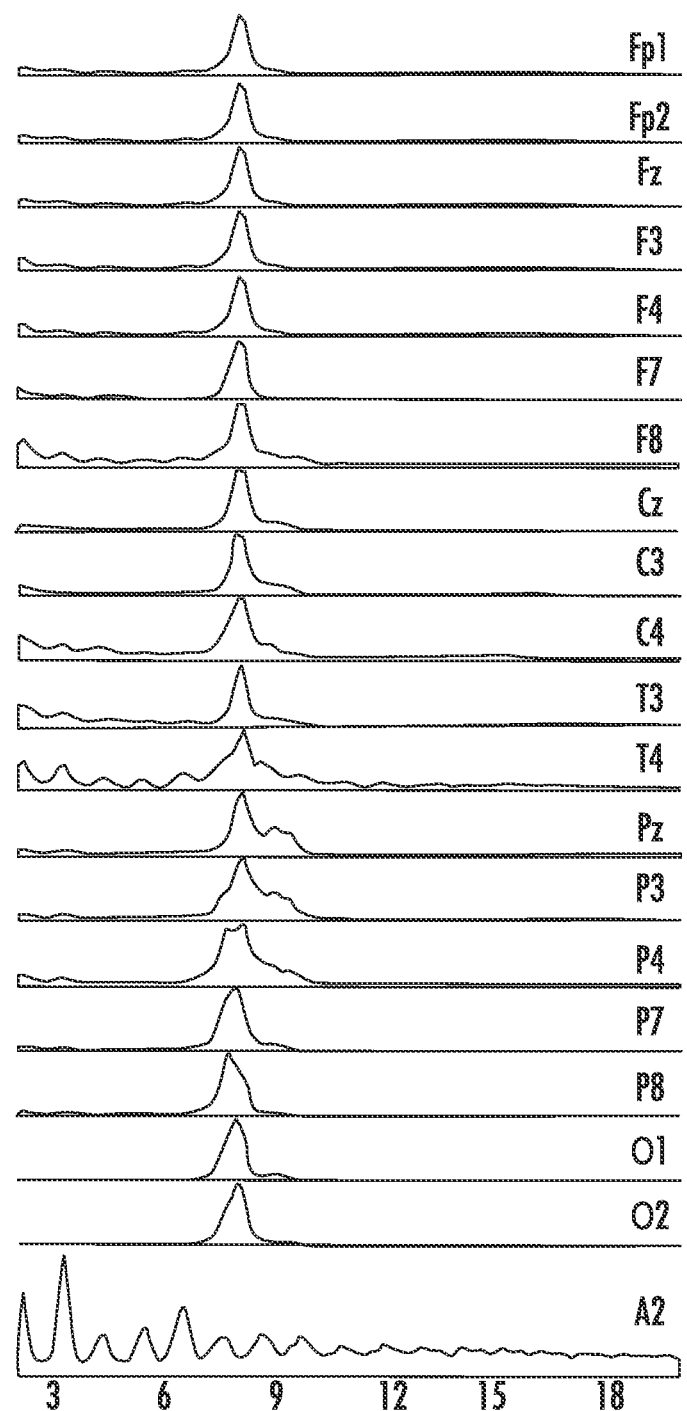

As noted elsewhere herein, brain arrhythmia has been proven to be a cause for many brain-related diseases and abnormal conditions. The Greatest Frequency is the frequency in which most neurons are firing at that portion of the brain (i.e., pertaining to the channel corresponding to that portion of the brain). Therefore, in order to make the substantially entire brain function at the same frequency, the Greatest Frequencies for each channel should be aligned toward the same frequency, which is referred to herein as the Target Frequency. Embodiments of the present disclosure utilize transcranial magnetic stimulation from a TMS system (see FIG. 7) to align the Greatest Frequencies of each channel to the Target Frequency. This is illustrated in FIG. 3B in which one or more treatments in accordance with embodiments of the present disclosure have been performed on the patient to eventually align the Greatest Frequencies for all of the channels.

A qEEG Report may be annotated so that each of the PSD plots has a corresponding indicator, such as color, to indicate in relative terms how close the Greatest Frequency of the brainwaves for a particular channel are to a desired frequency, i.e., the Target Frequency. If the Greatest Frequency of the brainwaves for a particular channel is substantially near (e.g., within a predetermined threshold difference) the Target Frequency, the PSD plot for that channel may be shown in a particular color (e.g., purple). A non-limiting exemplary color-coding scheme that may be used to display the PSD plots in a qEEG Report is summarized in Table 1.

TABLE 1

| COLOR | DIFFERENCE BETWEEN GREATEST FREQUENCY AND TARGET FREQUENCY (Hz) |
| --- | --- |
| Purple | Less than 0.1 |
| Blue | Between 0.1 and 2.5 |
| Green | Between 2.5 and 5 |
| Yellow | Between 5 and 7.5 |
| Red | 7.5 or Greater |

The color coding in the qEEG Report may be based on the difference between Greatest Frequency and Target Frequency for each channel. The color coding captures how aligned the Greatest Frequency is with the desired Target Frequency, and may thus enhance the qEEG Report to the treating physician and the patient. Persons of ordinary skill in the art will recognize that any other suitable visualization scheme may be utilized instead of color, such as shades of grey, shading patterns, labels, etc.

Figure 4:
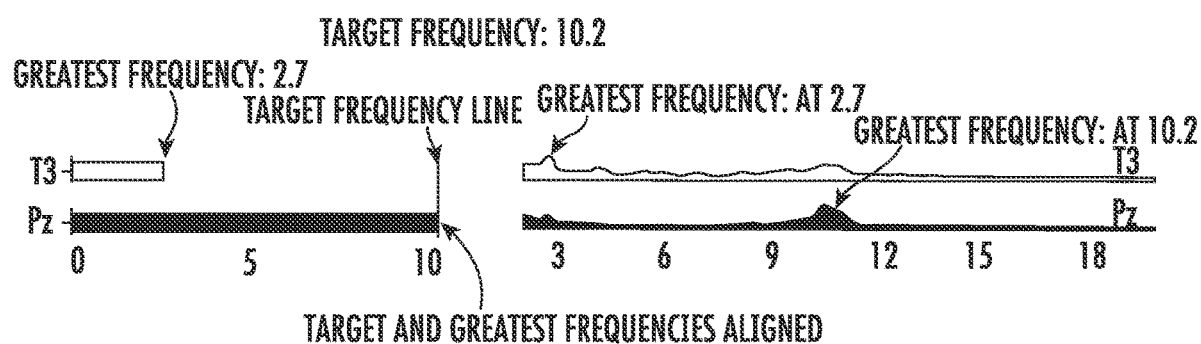
FIG. 4 represents a non-limiting example of a comparison of a sample patient's Greatest Frequency to a Target Frequency for a couple of channels.

The example illustrated in FIG. 4 explains an exemplary color-coding scheme. In this non-limiting example, it has been determined that the Target Frequency for this patient is 10.2 Hz. As can be seen, the patient's PSD plot for the T3 channel is recorded to have a Greatest Frequency of 2.7 Hz. Therefore, it can be determined that there is an irregular brainwave in this portion of the patient's brain. The current Greatest Frequency for the Pz channel is recorded to be 10.2 Hz, which coincides with the Target Frequency line. It can be determined that this portion of the patient's brain is functioning well. The difference between the Greatest Frequency and the Target Frequency for the T3 channel is 7.5 Hz, and 0 Hz for the Pz channel. As a result, the displayed or printed out qEEG Report for the patient may have a red color for representing the T3 channel and a purple color for representing the Pz channel.

A qEEG Report such as the example illustrated in FIG. 3A may be generated for each qEEG performed on the patient. As demonstrated with respect to the example of FIG. 4, each qEEG Report may be utilized to identify "brain arrhythmia" (i.e., irregular brainwave frequencies that are not aligned with the determined Target Frequency of the patient). In accordance with embodiments of the present disclosure, for different zones of the brain (e.g., channels as recorded by electrodes identified in the 10-20 system), the recorded Greatest Frequency is compared with the Target Frequency, which has been determined to be the frequency in which the patient's brain should be functioning. In addition to the qEEG Report, the recorded Greatest Frequencies pertaining to each channel may be output (e.g., displayed and/or printed) by bar plots. FIG. 4 illustrates only a couple of such bar plots (i.e., pertaining to the channels T3 and Pz), but a bar plot may be produced for each of the channels.

In those cases where all neurons in the brain are firing synchronously with the same frequency falling in the Alpha brainwave region, the recorded Greatest Frequency for each of the channels should coincide with the Target Frequency line. In FIG. 4, the Greatest Frequency is substantially aligned with the Target Frequency for the channel Pz. FIG. 3B illustrates where the Greatest Frequencies of all of the channels are substantially aligned.

If there is irregular brainwave frequency for some portion of the patient's brain, then the Greatest Frequency bar will not coincide with the Target Frequency line, which is depicted for the channel T3. As described with respect to FIG. 4, the bars may be colored based on how close the Greatest Frequency is to the Target Frequency, as per Table 1, though any other distinguishing aspect may be used (e.g., different grey shades, patterns, etc.).

Essentially, embodiments of the present disclosure infuse the patient's homeostatic energy into each area of the brain that is out of sync with the patient's homeostatic frequency, thus creating neuro-modulation so all neurons fire harmoniously. If a patient's brain rhythm in Alpha state is unbalanced, then this unbalance can lead to one or more mental disorders as described herein. As previously noted, embodiments of the present disclosure utilize transcranial magnetic stimulation from a TMS system to align the Greatest Frequencies of each channel to the Target Frequency in order to essentially "balance" the brain rhythm (e.g., see FIG. 3B).

Figure 5:
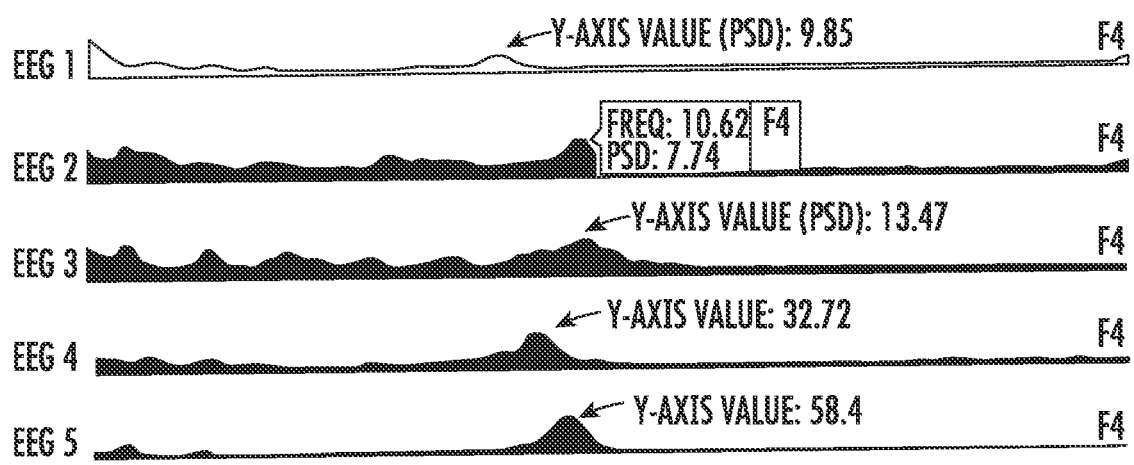
FIG. 5 illustrates a non-limiting example of an Overall Progress Grouped Chart depicting comparisons of a greatest Power Spectral Density ("PSD") value for a particular channel corresponding to EEG measurements of a sample patient over a series of different dates.

Referring to FIG. 5, an Overall Progress Grouped Chart can be output to show the greatest value of y-axis (PSD) of frequency in a range 7 Hz-13 Hz for a particular channel, which can be used to compare and contrast with qEEG measurements of different dates. For example, suppose five EEG examinations were taken for a patient over a period of time (depicted in FIG. 5 as EEG 1, EEG 2, EEG 3, EEG 4, and EEG 5), and considering only one channel for simplicity, in this case the F4 channel, the Overall Progress Grouped Chart depicts how the Greatest Frequency (corresponding to the maximum PSD) for the channel F4 moved over time.

As described with respect to FIG. 1, after one or more initial qEEG measurements have been made on a patient (see the process block 101), a mental state of the patient is diagnosed in the process block 102.

Diagnosing a patient according to conventional techniques and methodologies requires time and proper information. Often times this information is skewed. The patient providing the answers to the clinician may be mentally ill or drug dependent, and therefore may be effectively "challenged" to accurately answer a question, or at times may be a poor historian due to the illness.

Embodiments of the present disclosure overcome such issues by providing an objective assessment of the patient through an analysis of the qEEG measurements, which indicates which areas of the patient's brain are negatively impacted by their particular mental state. In accordance with certain embodiments, traditional psychometric assessments may also be given to the patient. Then, the results of such psychometric assessments may be compared with the objective assessment.

As previously described with respect to FIGS. 3A-4, the objective assessment involves recording qEEG measurements of the patient's brain activity, which can then be represented as a bar graph. For example, if the bar graph shows that the Greatest Frequencies for the Fp1, Fp2, Fz, F3, and F4 channels are below a baseline balance, then the patient may be diagnosed with ADHD. If desired, the practitioner can confirm this diagnosis with one or more traditional psychometric assessments, which may be administered prior to the qEEG and recorded by the software. The bar graph may be compared to the patient's answers. This may also be confirmed using the DSM-5. Such a more informed diagnosis allows psychiatrists to medicate correctly and licensed clinicians to deploy the proper therapeutic intervention, which can save months of diagnostic gathering, which could result in a wrong diagnosis. Furthermore, embodiments of the present disclosure provide practitioners an objective view of the brain movement overtime enabling them to determine if the patient answered the subjective psychometric assessments incorrectly.

Applicant has determined that there are distinctive qEEG Reports that correlate to particular mental states. This was confirmed after conducting hundreds of qEEG measurements on numerous different patients. In other words, characteristics of particular mental states correspond to certain identifiable recorded PSD measurements within a qEEG Report, and thus, embodiments of the present disclosure are capable of diagnosing with significant accuracy a mental state of a patient as a function of the qEEG Report produced by conducting qEEG measurements on the patient. For example, the following mental states can be diagnosed in a patient based on these characteristics of the qEEG Report:

Anxiety

Persons with anxiety disorders frequently have intense, excessive and persistent worry and fear about everyday situations. Often, anxiety disorders involve repeated episodes of sudden feelings of intense anxiety and fear or terror that reach a peak within minutes (panic attacks). These feelings of anxiety and panic interfere with daily activities, are difficult to control, are out of proportion to the actual danger, and can last a long time. Such persons may avoid places or situations to prevent these feelings. Symptoms may start during childhood or the teen years and continue into adulthood.

1. Indication: The graph on the right side of the Greatest PSD for one or more channels is "thick" as determined below.
2. "Thickness" is determined for each of these channels by averaging the PSD values in a range of 1 Hz through 5 Hz to the right of the Greatest Frequency, wherein the average PSD is calculated as a percentage of the recorded PSD at the Greatest Frequency for each of the F4 through P4 channels. (For example, if the Greatest Frequency is recorded to be 9 Hz at channel F4, the mean of the recorded PSD values from 10 Hz to 14 Hz would be converted into a percentage of the recorded PSD at the Greatest Frequency at channel F4.)
3. The calculated PSD percentages for channels F4 through P4 are then averaged. If this average is greater than or equal to 25%, then Anxiety is indicated (e.g., diagnosed) for this patient.

Depression

Depression is a mood disorder that causes a persistent feeling of sadness and loss of interest. Also called major depressive disorder or clinical depression, it affects how one feels, thinks, and behaves, and can lead to a variety of emotional and physical problems. Many have trouble performing normal day-to-day activities, and sometimes may feel as if life is not worth living.

1. Indication: PSDs for one or more channels (e.g., the Fp1, Fp2, Fz, F3, F4, F7, F8, Cz, C3, C4, T3, T4, and Pz channels) on left side of the Greatest Frequency is "thick" as determined below.
2. "Thickness" is determined for each of these channels by averaging the PSD values in a range of 1 Hz through 5 Hz to the left of the Greatest Frequency, wherein the average PSD is calculated as a percentage of the recorded PSD at the Greatest Frequency for each of the FP1 through O2 channels. (For example, if the Greatest Frequency is recorded to be 9 Hz at channel F4, the mean of the recorded PSD values from 4 Hz to 8 Hz would be converted into a percentage of the recorded PSD at the Greatest Frequency at channel F4.)
3. The calculated PSD percentages for channels FP1 through O2 are then averaged. If this average is greater than or equal to 25%, then Depression is indicated (e.g., diagnosed) for this patient.

Post-Traumatic Stress Disorder ("PTSD")

1. Indication: Relatively low PSD values across entire frequency spectrum at particular channels, wherein relatively low is determined as described below.
2. This is indicated at channels F8 and T4.
3. The mean of the recorded PSD values is calculated across entire frequency spectrum for each of channels F8 and T4. The mean for each is then converted to a percentage using the average of the PSD values at the Greatest Frequencies for all other channels.

4. These PSD values calculated at channels F8 and T4 are then averaged together. If this average is less than or equal to 25% of the mean Greatest Power percentage for all other channels, then PTSD is indicated (e.g., diagnosed).

Attention Deficit Hyperactivity Disorder ("ADHD")

1. Indication: Relatively low PSD values across entire frequency spectrum at particular channels, wherein relatively low is determined as described below.
2. This is indicated at channels Fp1, Fp2, Fz, F3, F4, and F7.
3. The mean of the recorded PSD values is calculated across entire frequency spectrum for each of channels Fp1, Fp2, Fz, F3, F4, and F7. The mean for each is then converted to a percentage using the average of the PSD values at the Greatest Frequencies for all other channels.
4. These PSD percentages calculated at channels Fp1, Fp2, Fz, F3, F4, and F7 are then averaged together. If this average is less than or equal to 25% of the mean Greatest Frequency percentage for all other channels, then ADHD is indicated (e.g., diagnosed).

Bi-Polar

1. Indication: Bi-polar is a mood disorder. There are two distinct and individual PSD elevations (peaks) at or within 4 Hz and 16 Hz. (This may be invalid if the patient is currently taking mood stabilizing medications and or drugs (e.g., Benadryl) or alcohol.)
2. This is indicated (e.g., diagnosed) at greater than or equal to 5 of the channels (e.g., 5 or more of the Fp1, Fp2, Fz, F3, F4, F7, F8, Cz, C3, C4, T3, T4, Pz, P3, P4, P7, P8, O1, and O2 channels).

Dementia

1. Indication: Greatest Frequency below 8 Hz.
2. This is indicated by the mean frequency across all channels being less than 8 Hz. This means that in a relaxed Alpha state, the patient demonstrates PSD values at a frequency lower than 8.2 Hz. This usually happens when a person is asleep.

Concussion/Traumatic Brain Injury ("TBI")

1. High-pointed spikes of approximately the same PSD at 6 Hz or less across six or more channels (e.g., six or more of the Fp1, Fp2, Fz, F3, F4, F7, F8, Cz, C3, C4, T3, T4, Pz, P3, P4, P7, P8, O1, and O2 channels). A high-pointed spike may be represented by narrow (e.g., width less than 0.3 Hz) elevated PSD values. Such groups of "spikes," also called clusters, occur when the natural homeostatic rhythm is disrupted by concussion or TBI, or a brain injury is so severe that the brain pattern is shifted and does not return to its natural homeostatic rhythm. The spikes can be in any six of the 19 channels/zones of the brain (location depends on where the brain was impacted).

Embodiments of the present disclosure are not limited to the foregoing mental states, and may also include tinnitus, short term memory issues, substance abuse disorder, sleep disorder, and a combination of depression and anxiety.

Referring to FIG. 10, in accordance with embodiments of the present disclosure, PSD characteristics particular to one or more mental states may be programmed into algorithms run in one or more software programs performed within a data processing system 1001. The EEG apparatus 1002, which may be used to make the EEG measurements, may be coupled (e.g., by a network connection) to the data processing system 1001 so that a qEEG Report can be produced by the data processing system 1001 so that the various PSD measurements can be analyzed by the algorithms to output a diagnosis of a mental state for a patient in accordance with the process block 102 of FIG. 1. Such algorithms may be programmed using any well-known programming language, including one that implements a machine learning system, as will be described in further detail herein. Alternatively, the EEG measurements may be entered into the data processing system 1001 as data files produced by the EEG apparatus 1002. Such data files may be in a "Brain Vision" format that includes the raw EEG data, a header file, and a marker file. The header file may include information about the number of channels, the number of data points, and the sampling interval used. The data files may include the raw EEG data in an IEEE Float32 format. The marker file may include information about the file name of the raw data file and the encoding used such as UTF-8. A Python library called "MNE" may be used to read the data files.

Before describing how embodiments of the present disclosure utilize iTMS to treat a patient for mental state(s) diagnosed in the process block 102, a TMS system 1003 will be described.

Transcranial magnetic stimulation ("TMS") is a noninvasive form of brain stimulation in which a changing magnetic field is used to cause electric current at a specific area of the brain through electromagnetic induction. An electric pulse generator, or stimulator, is connected to a magnetic coil, which in turn is connected to the scalp. The stimulator generates a changing electric current within the coil which induces a magnetic field; this field then causes a second inductance of inverted electric charge within the brain itself. Based on the principle of electromagnetic induction, TMS modulates the brain's electrical environment using magnetic fields, which pass through the scalp and skull unimpeded. These fields are produced by passing rapidly alternating electrical currents through a coil with a ferromagnetic core (i.e., an electromagnet in lieu of a permanent magnet). The magnetic field strength produced by TMS may vary from 1.5 to 3 teslas (T), and is comparable to an MRI device, except that it focuses on a limited area of the cortex using a circular, figure-eight, conical, or helmet-like coil design (e.g., H-coil). TMS can be administered in single pulses or as a brief series of pulses, called a train, for research, diagnostic, and therapeutic purposes. When used clinically, several thousand pulses may be applied over a period of minutes to hours. This is referred to as repetitive transcranial magnetic stimulation or "rTMS." These pulses can be delivered in a rapid (i.e., >1-20 Hz) repetitive fashion, enhancing cortical activity; or in a slow (i.e., <1 Hz) repetitive fashion, inhibiting cortical activity.

Figure 7:
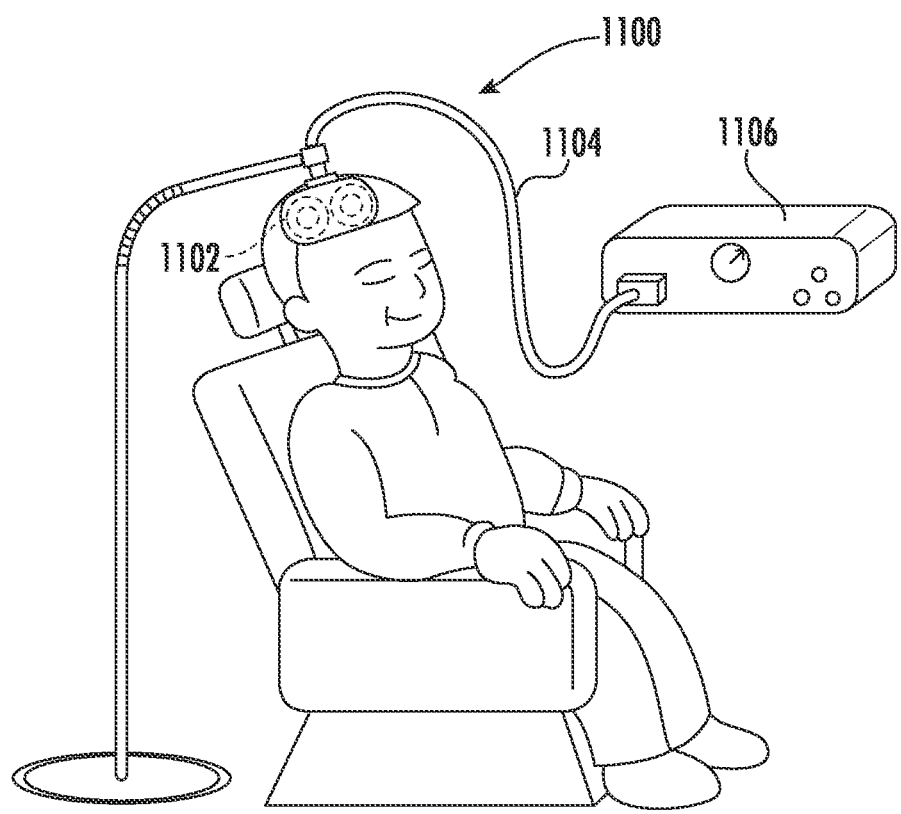
FIG. 7 illustrates a schematic diagram of a TMS system.

As shown in FIG. 7, a typical TMS system 1100 includes a stimulation coil (magnetic field generation means) 1102 and a magnetic stimulation control unit 1106 electrically connected to the stimulation coil 1102 through a cable 1104. The TMS system 1100 is designed to treat and/or ease certain symptoms by applying magnetic stimulation with certain intensity into the cranial nerve of the patient by means of the stimulation coil 1102 positioned in proximity to the scalp of the patient.

The stimulation coil 1102 is designed so that it can generate a variable magnetic field, which applies the magnetic stimulation onto at least specific positions of the patient (i.e., in proximity to selected zone of the patient's brain). Various types of conventional magnetic coils are available for the stimulation coil 1102. For example, the stimulation coil 1102 may be configured as a so-called figure eight-shape coil having a configuration made by placing two spiral coils on the same plane in the form of a number eight. This allows that an application of electric current to this figure eight-shaped coil in the same direction as shown in the drawing, for example, generates the maximum inductive current density immediately beneath the overlapped portions of the spirals.

The magnetic stimulation control unit 1106, which is designed to control an application of electric current pulses to the stimulation coil 1102, may use any one of several conventional units. The magnetic stimulation control unit 1106 may be manually operated by an operator. In the operation, the operator can control various settings such as magnitude and/or waveform of the current pulses determining the intensity of magnetic stimulation and/or the stimulation cycle or interval stimulation (e.g., the Pulse Rate, Train, and InterTrain) with a TMS system. The software produces a custom protocol of the Pulse Rate, Train and Intertrain.

Referring again to FIG. 1, embodiments of the present disclosure utilize the mental state diagnosis of the patient determined in the process block 102 to determine a treatment plan for treating certain selected zone(s) (process block 103).

In accordance with embodiments of the present disclosure, to begin the objective assessment for a diagnosis of a patient's mental state, the Target Frequency is determined. A set of qEEG measurements may be used to determine the Target Frequency. In accordance with embodiments of the present disclosure, the Target Frequency is the maximum recorded frequency at which the patient's brain effectively operates, and will be used to establish the target Target Frequency for other zones (e.g., EEG channels of the brain). As described herein, a goal is to improve frequency alignment across all brain zones. In other words, to achieve the "Homeostatic Frequency" for that patient's brain throughout all or at least desired zones.

The initial EEG measurements are converted into a representational graph (i.e., the PSD report) that shows where the patient's brain is balanced and where deficits exist, such as described herein with respect to FIGS. 3A-5. This may be followed by a face-to-face consult with the patient, and determination of the optimal "target" wave frequency (i.e., the Target Frequency to achieve for each of the zones) and how the "target" can change with time. Embodiments of the present disclosure are able to capture this information and then create a treatment plan (process block 103). After the Target Frequency is ascertained, in the process block 104, the patient undergoes iTMS treatment with the TMS system 1003, which may be performed using one or more various standard iTMS protocols, such as described herein.

Referring to the Brain Map diagram of FIG. 2, as previously noted, these are particular regions (zones) of the brain in which EEG channels may be utilized to measure brainwave activity. There are numerous brainwaves, measured in hertz (Hz), constituted on an EEG to include Delta, Theta, Alpha, Beta, and Gamma waves, which transition from low to high frequency, respectively. Embodiments of the present disclosure utilize iTMS to specifically target Alpha brainwaves. Often people with depression, anxiety, substance use, ADHD, OCD, and so forth commonly have elevated brainwaves outside the Alpha range and often have a suppression with the Alpha brainwaves. Elevation and suppression of brainwaves relates to the amplitude, represented on the y-axis where frequency remains on the x-axis. In accordance with embodiments of the present disclosure, each patient's Homeostatic Frequency is observed from the brainstem to the prefrontal cortex. This allows a tailored approach created by the software in the data processing system 1001 to stimulate this unique frequency and increase amplitude with the utilization of magnetic stimulation from the TMS system 1003.

The treatment plan as performed by the process block 104 attempts to bolster the patient's Homeostatic Frequency across some or all of the channels by addressing three to five regions (zones) in the brain: the CZ (central zone), the FZ (frontal zone), the F3 (dorsal lateral prefrontal cortex) zones, F4 (right dorsal lateral prefrontal cortex) zone, and FPZ (Frontal Parietal Zone), which may be performed in this order of treatment. It should be noted that these areas of the brain have not been used in typical TMS treatments, since it was believed that stimulating the CZ zone would induce seizures. Treating these locations in accordance to embodiments described herein substantiates growth of the Alpha brainwaves from the most primitive to the most advanced (i.e., back to front of the brain, respectively). Progressively, this decreases the amplitude of sedative and/or activating wavelengths outside the Homeostatic Frequency range while increasing the individualized amplitude within the Homeostatic Frequency range; this maximizes the patient's brain potential to improve and maintain rational thought and decrease many symptoms of depression, anxiety, alcohol/substance cravings, and improve sleep.

In accordance with embodiments of the present disclosure, the normal amplitude for the treatments under the standard protocols may be:

CZ Zone=5% to 25%
FZ Zone=5% to 25%
F3 Zone=5% to 25% iTMS has three standard protocols: First set of 10 treatments (Standard Protocol 1); second set of 10 treatments (Standard Protocol 2); and third set of 10 treatments (Standard Protocol 3).

For example, a first standard iTMS protocol may be composed of performing a selected number (e.g., ten) iTMS treatments that initiate with 40 total Trains, each of which is 10 seconds long, and with a frequency as determined from the Target Frequency (e.g., the Target Frequency+1 Hz). Between each of the Trains there is a break of 30 seconds where no magnetic impulses are introduced (i.e., the Inter-Train interval).

In accordance with embodiments of the present disclosure, the CZ zone is treated with 15 Trains, the FZ zone is treated with 20 Trains, and the F3 zone is treated with 5 Trains. Each treatment may be performed once daily but there are cases where two treatments may occur with a three-hour break between treatments.

After the 10 treatments, another qEEG takes place (process block 105), which may be accompanied with traditional psychometric testing. In the process block 106, the qEEG Reports are compared to identify progress such as described herein with respect to FIGS. 3A-5. In the process block 107, the process blocks 104-106 may be repeated any desired number of times to achieve a desired result (e.g., produce a uniformed Homeostatic Frequency in all measured zones of the brain (e.g., one or more, or even all, of the channels), maximize amplitudes of these frequencies, and decrease variability outside of the 8 Hz-12 Hz range). In accordance with embodiments of the present disclosure, each subsequent set of standard protocols may be performed in the same manner as the previous protocol except that the InterTrain is decreased for each of the CZ, FZ, and F3 zones (e.g., in ten second increments).

Note that after performing a treatment in accordance with a process block 104, the Target Frequency may adjust to a higher or lower hertz within the 8 Hz-12 Hz range.

A goal is to produce a uniformed Homeostatic Frequency in all measured zones of the brain, maximize amplitude of said frequencies, and decrease variability outside of the 8 Hz-12 Hz range. However, alignment of the heart (channel A2) with the transcending zones of the brain prove fruitful in context to overall balance and uniformity of the brain. At times, the patient may appear unbalanced as the heart rate does not align with all other zones of the brain per EEG. In this case, the average between the discrepancies act as the new target frequency for the subsequent 10 iTMS treatments.

Based on psychometric assessments, qEEGs, and PSD reports, embodiments of the present disclosure may adapt to different treatment locations and may require adjustment from the standard protocol, especially if the cortical zones of the summary graph remain subdued with little amplitude. This is largely related to underlining depression, anxiety. In these cases, the protocol starts with 300 pulses at F3 at 30% amplitude on the magnet; essentially this would change the protocol to one train per second for 300 pulses for 10 treatments. Then another EEG and psychometric assessments take place to evaluate any deviations and growth of the cortical zone or improvements of depressive and/or anxiety symptoms. This new treatment protocol continues for two rounds of 10 treatments which may include adjustment in the frequency depending on the EEG and alignment of all leads with the heart rate (A2 lead). On this protocol, only one treatment occurs over 24 hours. If this does not lead to a reduction in psychometric scores or increased movement in summary graph results, the F3 zone is changed to the F4 zone of the brain for stimulation implementing the same protocol: 300 pulses, one train per second, at 30% amplitude of the strength of the magnet. Again, only one treatment occurs within 24 hours when implementing this protocol. Another qEEG summary graph and psychometric screening panel is complete after 10 treatments; research has shown there are only two rounds of 10 treatments with this protocol. This is because balance in zones of the brain is being obtained with the protocol.

If the frontal cortex of the brain is not building, an additional protocol may be deployed after 30 treatments treating FpZ. The software will add this location if the EEG and FP1 and FP2 leads demonstrate limited amplitude after extended treatments, as outlined above, the incorporation of the FPZ location may demonstrate efficacy. Additionally, this tends to work well with patients who experience poor impulse control, hyperactivity, decreased concentration, irritability and chronic substance dependence. After attempts of treating both F3 and F4, as described above, the addition of FPZ in place of the these at 5 trains with a 15% amplitude of the strength of the magnet for 10 treatments (one every 24 hours) is utilized.

Embodiments of the present disclosure are applicable to the diagnosis and treatment of all neurological or mental disease states, including, but not limited to, Major Depressive Disorder ("MDD"), addictions of various types, anxiety, sleep disorders, substance abuse, traumatic brain injury/concussion, Attention Deficit Hyperactivity Disorder ("ADHD"), issues associated with menopause, executive functions, early onset Dementia, eating disorders, tinnitus, anger problems, short-term memory loss, Obsessive-Compulsive Disorder ("OCD"), migraines, improvement of athletic performance, balance problems, pain disorders, and other brain disorders.

In accordance with embodiments of the present disclosure, and as also described herein, processes performed within the data processing system 110 are configured to perform certain aspects as described with respect to the process blocks of FIG. 1 and produce outputs as described with respect to FIGS. 3A-5. As will be appreciated by one skilled in the art, aspects of the present disclosure may be embodied as a system, method, process, and/or program product. Accordingly, aspects of the present disclosure may take the form of an entirely hardware embodiment, an entirely software embodiment (including firmware, resident software, micro-code, etc.), or embodiments combining software and hardware aspects that may all generally be referred to herein as a "circuit," "circuitry," or "system." Furthermore, aspects of the present disclosure may take the form of a program product embodied in one or more computer-readable storage medium(s) having computer-readable program code embodied thereon. (However, any combination of one or more computer-readable medium(s) may be utilized. The computer-readable medium may be a computer-readable signal medium or a computer-readable storage medium.)

A computer-readable storage medium may be, for example, but not limited to, an electronic, magnetic, optical, electromagnetic, infrared, biologic, atomic, or semiconductor system, apparatus, controller, or device, or any suitable combination of the foregoing. More specific examples (a non-exhaustive list) of the computer-readable storage medium may include the following: an electrical connection having one or more wires, a portable computer diskette, a hard disk, a random access memory ("RAM"), a read-only memory ("ROM"), an erasable programmable read-only memory ("EPROM" or Flash memory), an optical fiber, a portable compact disc read-only memory ("CD-ROM"), an optical storage device, a magnetic storage device, or any suitable combination of the foregoing. In the context of this document, a computer-readable storage medium may be any tangible medium that can contain or store a program for use by or in connection with an instruction execution system, apparatus, controller, or device. Program code embodied on a computer-readable signal medium may be transmitted using any appropriate medium, including but not limited to wireless, wire line, optical fiber cable, RF, etc., or any suitable combination of the foregoing.

A computer-readable signal medium may include a propagated data signal with computer-readable program code embodied therein, for example, in baseband or as part of a carrier wave. Such a propagated signal may take any of a variety of forms, including, but not limited to, electro-magnetic, optical, or any suitable combination thereof. A computer-readable signal medium may be any computer-readable medium that is not a computer-readable storage medium and that can communicate, propagate, or transport a program for use by or in connection with an instruction execution system, apparatus, controller, or device.

The flowchart diagram and block diagrams in the figures illustrate architecture, functionality, and operation of possible implementations of systems, methods, processes, and program products according to various embodiments of the present disclosure. In this regard, each block in the flowchart diagram or block diagrams may represent a module, segment, or portion of code, which includes one or more executable program instructions for implementing the specified logical functions. It should also be noted that, in some implementations, the functions noted in the blocks may occur out of the order noted in the figures. For example, two blocks shown in succession may, in fact, be executed substantially concurrently, or the blocks may sometimes be executed in the reverse order, depending upon the functionality involved.

Modules implemented in software for execution by various types of processors may, for instance, include one or more physical or logical blocks of computer instructions which may, for instance, be organized as an object, procedure, or function. Nevertheless, the executables of an identified module need not be physically located together, but may include disparate instructions stored in different locations which, when joined logically together, include the module and achieve the stated purpose for the module. Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices. The data may provide electronic signals on a system or network.

These program instructions may be provided to a processor and/or controller of a general-purpose computer, special purpose computer, or other programmable data processing apparatus (e.g., controller) to produce a machine, such that the instructions, which execute via the processor of the computer or other programmable data processing apparatus, create means for implementing the functions/acts specified in the flowchart and/or block diagram block or blocks.

It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions. For example, a module may be implemented as a hardware circuit comprising custom VLSI circuits or gate arrays, off-the-shelf semiconductors such as logic chips, transistors, controllers, or other discrete components. A module may also be implemented in programmable hardware devices such as field programmable gate arrays, programmable array logic, programmable logic devices, or the like.

Computer program code, i.e., instructions, for carrying out operations for embodiments of the present disclosure may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network ("LAN") or a wide area network ("WAN"), or the connection may be made to an external computer (for example, through the Internet using an Internet Service Provider).

These program instructions may also be stored in a computer-readable storage medium that can direct a computer, other programmable data processing apparatus, controller, or other devices to function in a particular manner, such that the instructions stored in the computer-readable medium produce an article of manufacture including instructions which implement the function/act specified in the flowchart and/or block diagram block or blocks.

The program instructions may also be loaded onto a computer, other programmable data processing apparatus, controller, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

One or more databases may be included in a host for storing and providing access to data for the various implementations. One skilled in the art will also appreciate that, for security reasons, any databases, systems, or components of the present disclosure may include any combination of databases or components at a single location or at multiple locations, wherein each database or system may include any of various suitable security features, such as firewalls, access codes, encryption, de-encryption and the like. The database may be any type of database, such as relational, hierarchical, object-oriented, and/or the like. Common database products that may be used to implement the databases include DB2 by IBM, any of the database products available from Oracle Corporation, Microsoft Access by Microsoft Corporation, or any other database product. The database may be organized in any suitable manner, including as data tables or lookup tables.

Association of certain data may be accomplished through any data association technique known and practiced in the art. For example, the association may be accomplished either manually or automatically. Automatic association techniques may include, for example, a database search, a database merge, GREP, AGREP, SQL, and/or the like. The association step may be accomplished by a database merge function, for example, using a key field in each of the manufacturer and retailer data tables. A key field partitions the database according to the high-level class of objects defined by the key field. For example, a certain class may be designated as a key field in both the first data table and the second data table, and the two data tables may then be merged on the basis of the class data in the key field. In these embodiments, the data corresponding to the key field in each of the merged data tables is preferably the same. However, data tables having similar, though not identical, data in the key fields may also be merged by using AGREP, for example.

Reference may be made herein to "configuring" a device. It should be understood that this may include selecting predefined logic blocks and logically associating them, such that they provide particular logic functions, which includes monitoring or control functions. It may also include programming computer software-based logic of retrofit control device, wiring discrete hardware components, or a combination of any or all of the foregoing.

Reference throughout this specification to "one embodiment," "embodiments," or similar language means that a particular feature, structure, or characteristic described in connection with the embodiments is included in at least one embodiment of the present disclosure. Thus, appearances of the phrases "in one embodiment," "in an embodiment," "embodiments," and similar language throughout this specification may, but do not necessarily, all refer to the same embodiment. Furthermore, the described features, structures, aspects, and/or characteristics of the disclosure may be combined in any suitable manner in one or more embodiments. Correspondingly, even if features may be initially claimed as acting in certain combinations, one or more features from a claimed combination can in some cases be excised from the combination, and the claimed combination can be directed to a sub-combination or variation of a sub-combination.

In the descriptions herein, numerous specific details are provided, such as examples of programming, software modules, user selections, network transactions, database queries, database structures, hardware modules, hardware circuits, hardware chips, controllers, etc., to provide a thorough understanding of embodiments of the disclosure. One skilled in the relevant art will recognize, however, that the disclosure may be practiced without one or more of the specific details, or with other methods, components, materials, and so forth. In other instances, well-known structures, materials, or operations may be not shown or described in detail to avoid obscuring aspects of the disclosure.

Figure 8:
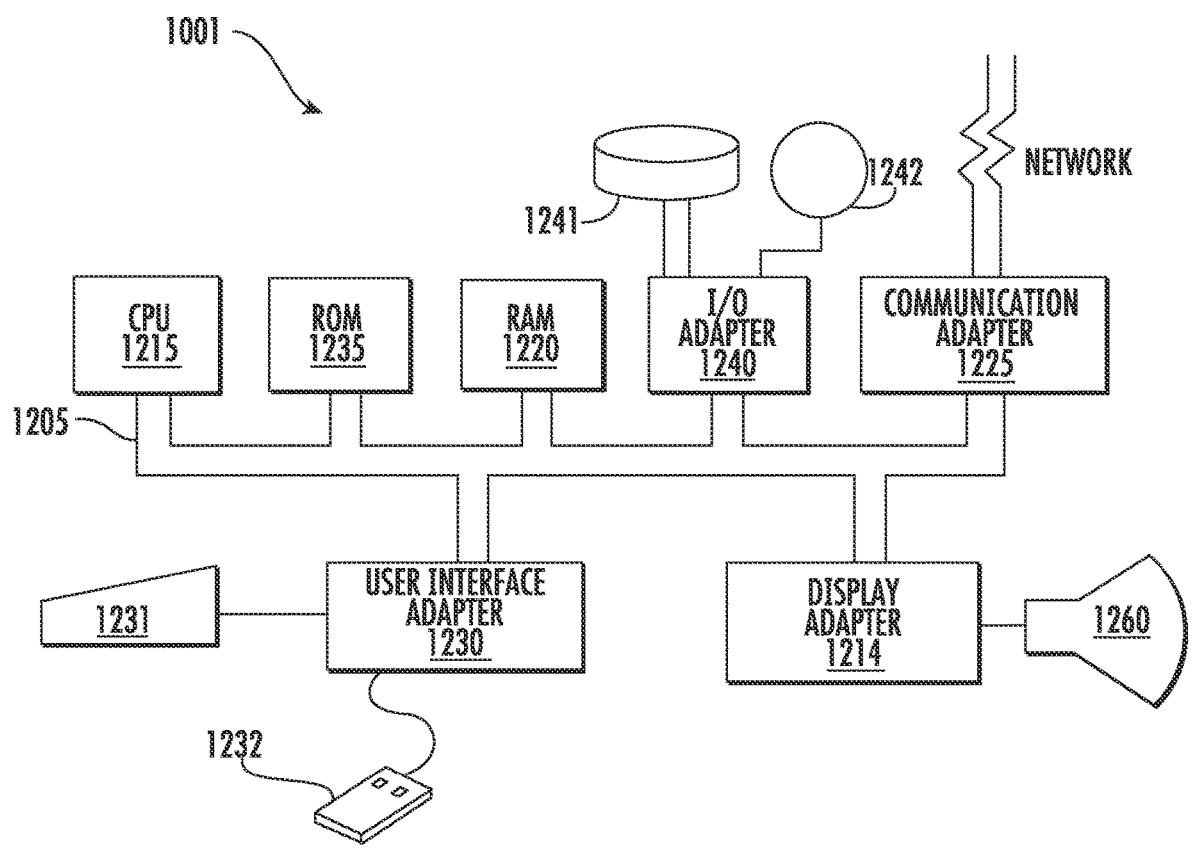
FIG. 8 illustrates a block diagram of a data processing system configured in accordance with embodiments of the present disclosure.

With reference now to FIG. 8, a block diagram illustrating a data processing system is depicted in which aspects of embodiments of the disclosure may be implemented. Data processing system 1001 may employ a peripheral component interconnect ("PCI") local bus architecture. Although the depicted example employs a PCI bus, other bus architectures such as Accelerated Graphics Port ("AGP") and Industry Standard Architecture ("ISA") may be used, among others. Processor 1215, volatile memory 1220, and non-volatile memory 1235 may be connected to the local bus 1205 through a PCI Bridge (not shown). The PCI Bridge also may include an integrated memory controller and cache memory for processor 1215. Additional connections to the local bus 1205 may be made through direct component interconnection or through add-in boards. In the depicted example, a LAN adapter 1225, small data processing system interface ("SCSI") host bus adapter (not shown), and expansion bus interface (not shown) may be connected to the local bus 1205 by direct component connection. In contrast, an audio adapter (not shown), a graphics adapter (not shown), and a display adapter 1214 and display 1260 may be coupled to the local bus 1205 by add-in boards inserted into expansion slots. A user interface adapter 1230 may provide a connection for a keyboard 1231 and a mouse 1232. An I/O adapter 1240 may provide a connection for a hard disk drive 1241, a tape drive, and a CD-ROM/DVD drive 1242.

An operating system may be run on processor 1215 and used to coordinate and provide control of various components within the data processing system 1001. The operating system may be a commercially available operating system. An object-oriented programming system such as Java may run in conjunction with the operating system and provide calls to the operating system from Java programs or programs executing on the system 1001. Instructions for the operating system, the object-oriented operating system, and programs may be located on the non-volatile memory 1235 storage devices, such as the hard disk drive 1241, and may be loaded into the volatile memory 1220 for execution by the processor 1215.

Those of ordinary skill in the art will appreciate that the hardware in FIG. 8 may vary depending on the implementation. Other internal hardware or peripheral devices, such as flash ROM (or equivalent nonvolatile memory) or optical disk drives and the like, may be used in addition to or in place of the hardware depicted in FIG. 8. Also, the processes of the present disclosure may be applied to a multiprocessor data processing system.

As another example, the data processing system 1001 may be a stand-alone system configured to be bootable without relying on some type of network communication interface, whether or not the data processing system 1001 includes some type of network communication interface. As a further example, the data processing system 1001 may be an embedded controller, which is configured with ROM and/or flash ROM providing non-volatile memory storing operating system files or user-generated data.

The depicted example in FIG. 8 and above-described examples are not meant to imply architectural limitations. Further, a computer program form of the present disclosure may reside on any computer-readable storage medium (i.e., floppy disk, compact disk, hard disk, tape, ROM, RAM, etc.) used by a data processing system. (The terms "computer," "system," and "data processing system" are used interchangeably herein.)

Reference may be made herein to a device, circuit, circuitry, system, or module "configured to" perform a particular function or functions. It should be understood that this may include selecting predefined logic blocks and logically associating them, such that they provide particular logic functions, which includes monitoring or control functions. It may also include programming computer software-based logic, wiring discrete hardware components, or a combination of any or all of the foregoing.

Reference throughout this specification to "an embodiment," "embodiments," "certain embodiments," "various embodiments," or similar language means that a particular feature, structure, or characteristic described in connection with the embodiments is included in at least one embodiment of the present disclosure. Thus, appearances of the phrases "in embodiments," "in an embodiment," "embodiments," "in certain embodiments," and similar language throughout this specification may, but do not necessarily, all refer to the same embodiment. Furthermore, the described features, structures, aspects, or characteristics of the disclosure may be combined in any suitable manner in one or more embodiments. Correspondingly, even if features may be initially claimed as acting in certain combinations, one or more features from a claimed combination can in some cases be excised from the combination, and the claimed combination can be directed to a sub-combination or variation of a sub-combination.

The terminology used herein is for the purpose of describing particular embodiments and applications only and is not intended to be limiting of the disclosure. In the descriptions herein, numerous specific details are provided, such as examples of activities, circumstances, services, faults, errors, responses, reactions, processor activities, operations, events, mechanisms, software threads, cyberattacks, signals, or actions, programming, software modules, designer, manufacturer, or end user selections, network transactions, database queries, database structures, hardware modules, hardware circuits, hardware chips, controllers, etc., to provide a thorough understanding of embodiments of the disclosure. One skilled in the relevant art will recognize, however, that the disclosure may be practiced without one or more of the specific details, or with other methods, components, materials, activities, circumstances, services, faults, errors, responses, reactions, processor activities, operations, events, mechanisms, software threads, cyberattacks, signals, and so forth. In other instances, well-known structures, materials, or operations may be not shown or described in detail to avoid obscuring aspects of the disclosure.

Benefits, advantages, and solutions to problems may have been described herein with regard to specific embodiments or applications. However, the benefits, advantages, solutions to problems, and any element(s) that may cause any benefit, advantage, or solution to occur or become more pronounced are not to be construed as critical, required, or essential features or elements of any or all the claims.

Those skilled in the art having read this disclosure will recognize that changes and modifications may be made to the embodiments without departing from the scope of the present disclosure. It should be appreciated that the particular implementations and applications shown and described herein may be illustrative of the disclosure and are not intended to otherwise limit the scope of the present disclosure in any way. Other variations may be within the scope of the following claims. Headings herein are not intended to limit the disclosure, embodiments of the disclosure, or other matter disclosed under the headings.

Herein, the term "or" may be intended to be inclusive, wherein "A or B" includes A or B and also includes both A and B. As used herein, the term "or" when used in the context of a listing of entities, refers to the entities being present singly or in combination. Thus, for example, the phrase "A, B, C, or D" includes A, B, C, and D individually, but also includes any and all combinations and sub-combinations of A, B, C, and D. As used herein, the term "and/or" when used in the context of a listing of entities, refers to the entities being present singly or in combination. Thus, for example, the phrase "A, B, C, and/or D" includes A, B, C, and D individually, but also includes any and all combinations and sub-combinations of A, B, C, and D.

As used herein, the singular forms "a," "an," and "the" may be intended to include the plural forms as well, unless the context clearly indicates otherwise.

The corresponding structures, materials, acts, and equivalents of all means or step plus function elements in the claims may be intended to include any structure, material, or act for performing the function in combination with other claimed elements as specifically claimed.

What is claimed is:

1. A method comprising:
    taking a first set of electroencephalography ("EEG") measurements at predetermined zones of a brain of a patient;
    producing a first quantitative EEG ("qEEG") report from the first set of EEG measurements, wherein the first qEEG report comprises Power Spectral Density ("PSD") values pertaining to each of the predetermined zones of the brain of the patient;
    analyzing one or more specified characteristics of the first qEEG report to diagnose a mental state of the patient;
    performing a first set of individualized transcranial magnetic stimulation ("iTMS") treatments on the patient in accordance with a first standard protocol, wherein the first standard protocol comprises applying transcranial magnetic stimulation to a Cz zone, a Fz zone, and an F3 zone of the brain of the patient, wherein the Cz, Fz, and F3 zones correspond to zones as designated within a 10-20 system of electrode placement, wherein a number of pulses of the applied transcranial magnetic stimulation to Cz, Fz, and F3 zones is dependent upon a first measured homeostatic frequency particular to the patient as determined by the first qEEG report;
    taking a second set of EEG measurements at the predetermined zones of the brain of the patient;
    producing a second qEEG report from the second set of EEG measurements;
    comparing the second qEEG report to the first qEEG report to evaluate progress in establishing the homeostatic frequency in desired zones of the brain of the patient; and
    performing a second set of iTMS treatments on the patient in accordance with a second standard protocol when the homeostatic frequency has not been satisfactorily established in the desired zones of the brain of the patient, wherein the second standard protocol comprises applying a second set of transcranial magnetic stimulation to the Cz, Fz, and F3 zones, wherein a number of pulses of the second set of transcranial magnetic stimulation applied to the Cz, Fz, and F3 zones of the second standard protocol is dependent upon a second measured homeostatic frequency particular to the patient as determined by the second qEEG report.

2. The method as recited in claim 1, wherein an intertrain interval of the second standard protocol is different than an intertrain interval of the first standard protocol.

3. The method as recited in claim 1, wherein the mental state is selected from a group consisting of traumatic brain injury, tinnitus, short term memory issues, substance abuse disorder, sleep disorder, anxiety, depression, post-traumatic stress disorder, attention deficit hyperactivity disorder, bi-polar disorder, dementia, sleep disorders and a combination of depression and anxiety.

4. The method as recited in claim 1, wherein the predetermined zones correspond to electrode placement of a 10-20 system, wherein the predetermined zones are selected from a group consisting of Fp1, Fp2, Fz, F3, F4, F7, F8, Cz, C3, C4, T3, T4, Pz, P3, P4, P7, P8, O1, and O2.

5. The method as recited in claim 4, wherein the analyzing results in a diagnosis of a specified mental state in response to determining that the PSD values pertaining to certain ones of the predetermined zones are relatively lower than at other ones of the predetermined zones.

6. The method as recited in claim 5, wherein the specified mental state is diagnosed to be post-traumatic stress disorder when the certain ones of the predetermined zones are F8 and T4.

7. The method as recited in claim 5, wherein the specified mental state is diagnosed to be attention deficit hyperactivity disorder when the certain ones of the predetermined zones are Fp1, Fp2, Fz, F3, F4, and F7.

8. The method as recited in claim 4, wherein the analyzing results in a diagnosis of a traumatic brain injury in response to identification of one or more peaks in the PSD values pertaining to a majority of the predetermined zones, the one or more peaks being identified at approximately less than or equal to 6 Hz.

9. A system comprising:
    an electroencephalography ("EEG") apparatus configured to take a first set of EEG measurements at predetermined zones of a brain of a patient and a second set of EEG measurements at the predetermined zones of the brain of the patient;
    circuitry configured to produce a first quantitative EEG ("qEEG") report from the first set of EEG measurements and a second qEEG report from the second set of EEG measurements, wherein the first qEEG report and the second report each comprises Power Spectral Density ("PSD") values pertaining to each of the predetermined zones of the brain of the patient;

circuitry configured to analyze one or more specified characteristics of the first qEEG report to diagnose a mental state of the patient;

circuitry configured to compare the second qEEG report to the first qEEG report to evaluate progress in establishing a homeostatic frequency in desired zones of the brain of the patient; and a transcranial magnetic stimulation ("TMS") system configured to:

perform a first set of individualized transcranial magnetic stimulation ("iTMS") treatments on the patient in accordance with a first standard protocol, wherein the first standard protocol comprises applying transcranial magnetic stimulation to a Cz zone, a Fz zone, and an F3 zone of the brain of the patient, wherein the Cz, Fz, and F3 zones correspond to zones as designated within a 10-20 system of electrode placement, the TMS system being configured so that a number of pulses of the applied transcranial magnetic stimulation to Cz, Fz, and F3 zones is dependent upon a first measured homeostatic frequency particular to the patient as determined by the first qEEG report, the second set of EEG measurements being taken after performance of the first set of iTMS; and perform a second set of iTMS treatments on the patient in accordance with a second standard protocol when the homeostatic frequency has not been satisfactorily established in the desired zones of the brain of the patient, wherein the second standard protocol comprises applying transcranial magnetic stimulation to the Cz, Fz, and F3 zones, wherein a number of pulses of the applied transcranial magnetic stimulation to the Cz, Fz, and F3 zones of the second standard protocol is dependent upon a second measured homeostatic frequency particular to the patient as determined by the second qEEG report.

10. The system of claim 9, wherein an intertrain interval of the second standard protocol is different than an intertrain interval of the first standard protocol.

11. The system of claim 9, wherein the mental state is selected from a group consisting of traumatic brain injury, tinnitus, short term memory issues, substance abuse disorder, sleep disorder, anxiety, depression, post-traumatic stress disorder, attention deficit hyperactivity disorder, bi-polar disorder, dementia, sleep disorders and a combination of depression and anxiety.

12. The system of claim 9, wherein the predetermined zones correspond to electrode placement of a 10-20 system, wherein the predetermined zones are selected from a group consisting of Fp1, Fp2, Fz, F3, F4, F7, F8, Cz, C3, C4, T3, T4, Pz, P3, P4, P7, P8, O1, and O2.

13. The system of claim 12, wherein the analyzing results in a diagnosis of a specified mental state in response to determining that the PSD values pertaining to certain ones of the predetermined zones are relatively lower than at other ones of the predetermined zones.

14. The system of claim 13, wherein the specified mental state is diagnosed to be post-traumatic stress disorder when the certain ones of the predetermined zones are F8 and T4.

15. The system of claim 13, wherein the specified mental state is diagnosed to be attention deficit hyperactivity disorder when the certain ones of the predetermined zones are Fp1, Fp2, Fz, F3, F4, and F7.

16. The system of claim 12, wherein the analyzing results in a diagnosis of a traumatic brain injury in response to identification of one or more peaks in the PSD values pertaining to a majority of the predetermined zones, the one or more peaks being identified at approximately less than or equal to 6 Hz.

* * * * *